(12) United States Patent
Bonutti et al.

(10) Patent No.: US 7,112,179 B2
(45) Date of Patent: Sep. 26, 2006

(54) ORTHOSIS

(75) Inventors: Boris P. Bonutti, Effingham, IL (US); Peter M. Bonutti, Effingham, IL (US); Kevin R. Ruholl, Effingham, IL (US)

(73) Assignee: Marc Tec, LLC, Effingham, IL (US)

( * ) Notice: Subject to any disclaimer, the term of this patent is extended or adjusted under 35 U.S.C. 154(b) by 19 days.

(21) Appl. No.: 10/795,892

(22) Filed: Mar. 8, 2004

(65) Prior Publication Data
US 2005/0197605 A1    Sep. 8, 2005

(51) Int. Cl.
*A61F 5/00*    (2006.01)
(52) U.S. Cl. ............................ 602/16; 602/21; 602/26; 602/27; 602/32
(58) Field of Classification Search .................. 602/16, 602/21, 26, 27, 32, 36
See application file for complete search history.

(56) References Cited

U.S. PATENT DOCUMENTS

| | | | | |
|---|---|---|---|---|
| 4,809,688 A | * | 3/1989 | Aymerica del Valle et al. | 602/21 |
| 5,376,091 A | * | 12/1994 | Hotchkiss et al. | 606/55 |
| 5,503,619 A | * | 4/1996 | Bonutti | 602/16 |
| 5,653,680 A | * | 8/1997 | Cruz | 602/21 |
| 5,772,619 A | * | 6/1998 | Corbett | 602/16 |
| 5,848,979 A | * | 12/1998 | Bonutti et al. | 601/5 |
| 5,882,323 A | * | 3/1999 | Belkin | 602/21 |
| 6,113,562 A | * | 9/2000 | Bonutti et al. | 602/20 |
| 6,142,964 A | * | 11/2000 | Gilmour | 602/20 |
| 6,599,263 B1 | * | 7/2003 | Bonutti et al. | 602/20 |

* cited by examiner

*Primary Examiner*—Henry Bennett
*Assistant Examiner*—Amanda Wieker
(74) *Attorney, Agent, or Firm*—Fleit Kain Gibbons Gutman Bongini & Bianco; Paul D. Bianco; Martin Fleit

(57) ABSTRACT

An orthosis for stretching tissue around a joint of a patient between first and second relatively pivotable body portions. The orthosis includes a first arm member affixable to the first body portion and including a first extension member extending therefrom. A second arm member affixable to the second body portion is also included and has a second extension member having an arcuate shape extending therefrom. The second extension member is operatively connected to the first extension member and travels trough the first extension member along an arcuate pat when the second arm member is moved from a first position to a second position relative to the first arm member.

28 Claims, 9 Drawing Sheets

ORTHOSIS

FIELD OF THE INVENTION

The present invention relates to an adjustable orthosis for stretching tissue in the human body. In particular, the present invention relates to an adjustable orthosis which can be used for stretching tissue such as ligaments, tendons or muscles around a joint during flexion or extension of the joint.

BACKGROUND OF THE INVENTION

In a joint, the range of motion depends upon the anatomy of that joint and on the particular genetics of each individual. Typically, joints move in two directions, flexion and extension. Flexion is to bend the joint and extension is to straighten the joint; however, in the orthopedic convention some joints only flex. For example, the ankle has dorsiflexion and plantarflexion. Other joints not only flex and extend, they rotate. For example, the elbow joint has supination and pronation, which is rotation of the hand about the longitudinal axis of the forearm placing the palm up or the palm down.

When a joint is injured either by trauma or by surgery, scar tissue can form, often resulting in flexion or extension contractures. Such conditions can limit the range of motion of the joint, limiting flexion (in the case of an extension contracture) or extension (in the case of a flexion contracture) of the injured joint. It is often possible to correct this condition by use of a range-of-motion (ROM) orthosis.

ROM orthoses are devices commonly used during physical rehabilitative therapy to increase the range-of-motion over which the patient can flex or extend the joint. Commercially available ROM orthoses are typically attached on opposite members of the joint and apply a torque to rotate the joint in opposition to the contraction. The force is gradually increased to increase the working range or angle of joint motion. Exemplary orthoses include U.S. Pat. No.: 6,599,263, entitled "Shoulder Orthosis;" U.S. Pat. No. 6,113,562, entitled "Shoulder Orthosis;" U.S. Pat. No. 5,848,979, entitled "Orthosis;" U.S. Pat. No. 5,685,830, entitled "Adjustable Orthosis Having One-Piece Connector Section for Flexing;" U.S. Pat. No. 5,611,764, entitled "Method of Increasing Range of Motion;" U.S. Pat. No. 5,503,619, entitled "Orthosis for Bending Wrists;" 5,456,268, entitled "Adjustable Orthosis;" U.S. Pat. No. 5,453,075, entitled "Orthosis with Distraction through Range of Motion;" U.S. Pat. No. 5,395,303, entitled "Orthosis with Distraction through Range of Motion;" 5,365,947, entitled "Adjustable Orthosis;" U.S. Pat. No. 5,285,773, entitled "Orthosis with Distraction through Range of Motion;" U.S. Pat. No. 5,213,095, entitled "Orthosis with Joint Distraction;" and U.S. Pat. No. 5,167,612, entitled "Adjustable Orthosis," all to Bonutti and herein are expressly incorporated by reference in their entirety.

SUMMARY OF THE INVENTION

The present invention provides an orthosis for stretching tissue around a joint of a patient between first and second relatively pivotable body portions. The joint and the first and second body portions defining on one side of the joint an inner sector which decreases in angle as the joint is flexed and defining on the opposite side of the joint an outer sector which decreases in angle as the joint is extended.

The orthosis includes a first arm member affixable to the first body portion. The first arm member has a first extension member extending at an angle $\alpha$ therefrom. A second arm member affixable to the second body portion is also included. The second arm member has a second extension member having an arcuate shape extending therefrom. The second and first extension members are operatively connected, such that the second extension member travels through the first extension member along an arcuate path when the second arm member is moved from a first position to a second position relative to the first arm member.

The orthosis further includes a drive assembly for selectively moving the second extension member relative to the first extension member. The drive assembly is mounted onto the first extension member, engaging the second extension member. The drive assembly can be manually or automatically actuated to selectively move the second extension member relative to the first extension member.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention relates to an orthosis for moving a joint between first and second relatively pivotable body portions. The joint and the first and second body portions define on one side (the flexor side) of the joint an inner sector which decreases in angle as the joint is flexed (bent) and on the opposite side (the extensor side) of the joint an outer sector which decreases in angle as the joint is extended (straightened). The orthosis of the present invention is affixable to either the flexor or extensor side of the joint for treatment of flexion or extension contractures.

Figure 1:
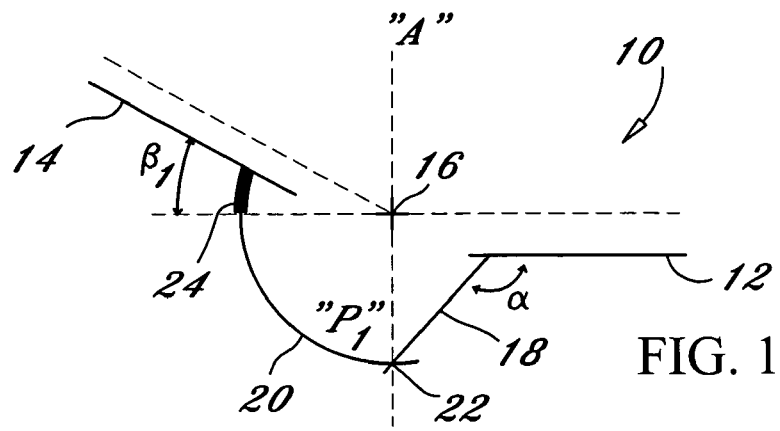
FIG. 1 is a schematic diagram of the orthosis of the present invention in a flexed position.

Referring now to the drawing figures in which like reference designators refer to like elements, there is shown in FIG. 1, a schematic of the orthosis 10 of the present invention. The orthosis 10 includes a first arm member 12 attachable to the first body portion and a second arm member 14 attachable to the second body portion, wherein a joint axis of rotation 16 is interposed between and offset from the first and second arm members 12 and 14. The first and second arm members 12 and 14 are operatively connected to each other offset from the joint axis 16.

The first arm member 12 of the orthosis 10 includes a first extension member 18, which extends at angle $\alpha$ from the first arm member 12. The second arm member 14 of the orthosis 10 includes a second extension member 20 extending therefrom and having an arcuate shape. The first and second extension members 18 and 20 are operatively connected at point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle $\alpha$ between the first extension member 18 and the first arm member 12 and the radius of curvature of the second extension member 20 are a function of the joint to be treated and the degree of flexion or extension contractures.

The orthosis further includes a drive assembly 22 at point "P." The drive assembly connects the first and second extension members 18 and 20 for applying force to the first and second arm members 12 and 14 to pivot the first and second body portions relative to each other about the joint.

Figure 2:
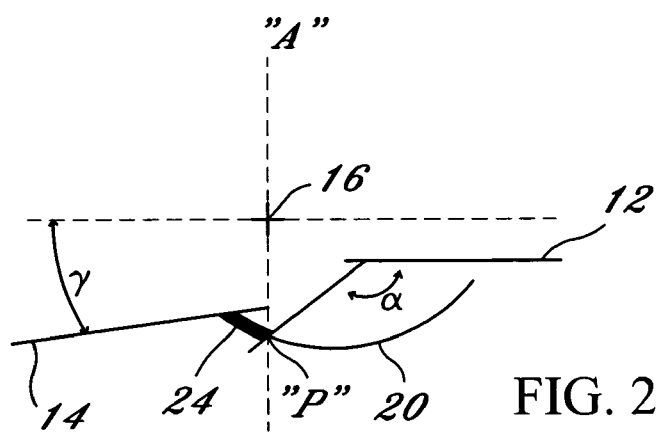
FIG. 2 is a schematic diagram of the orthosis of the present invention in an extended position.

The orthosis 10 of the present invention is shown having an angle $\alpha$ such that the operative connection, at point "P," of the first and second extensions 18 and 20 is located in a plane "A" passing through the joint axis 16, wherein plane "A" is substantially orthogonal to a longitudinal axis of the first arm member 12. This position of point "P" provides an angle $\beta_1$ between the second arm member 14 and the joint axis 16, wherein $\beta_1$ is the maximum angle of flexion. As shown in FIG. 2, the second extension member includes a stop 24. The stop 24 acts to limit the angle of maximum extension $\gamma$ between the second arm member 14 and the joint axis 16. An increase in the length of the stop 24 will decrease the angle of maximum extension $\gamma$. A decrease in the length of the stop 24 will increase the angle of maximum extension $\gamma$.

Figure 3:
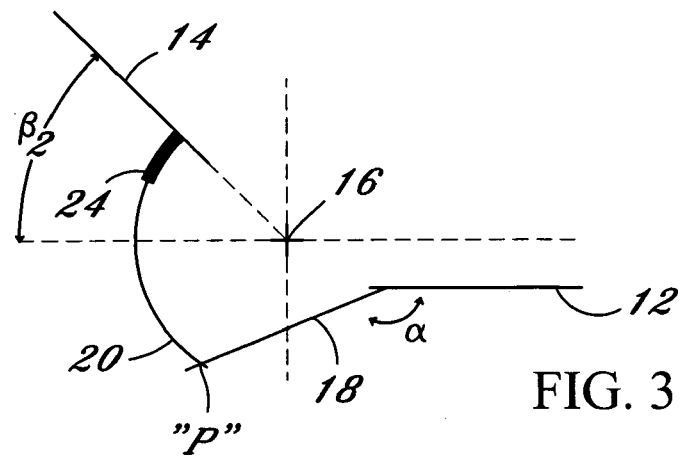
FIG. 3 is a second schematic diagram of the orthosis of the present invention in a flexed position.

Referring to FIG. 3, the maximum flexion angle can be increased by increasing the angle $\alpha$. An increase in the angle $\alpha$ will move the point "P" to a location "in front of" the plane "A." This position of point "P" provides an angle $\beta_2$ between the second arm member 14 and the joint axis 16 in maximum flexion, wherein $\beta_2$ is greater than $\beta_1$. The greater the angle $\alpha$ the greater the angle of maximum flexion.

Alternatively, (not shown) a decrease in the angle $\alpha$ will move the point "P" to a location "behind" the plane "A." This position of point "P" provides an angle $\beta_3$ between the second arm member 14 and the joint axis 16 in maximum flexion, wherein $\beta_3$ is less than $\beta_1$. The smaller the angle $\alpha$, the smaller the angle $\beta$ of maximum flexion.

Figure 4:
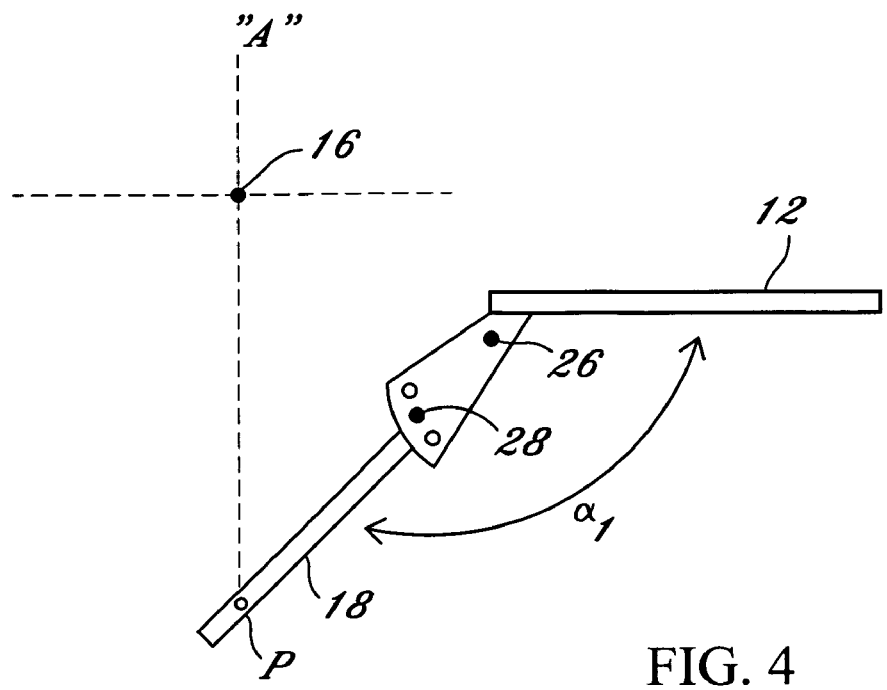
FIG. 4 shows an adjustable first extension member of the orthosis of the present invention.

Referring to FIG. 4, the first extension member 18 is selectively, pivotally connected at location 26 to the first arm member 12. The pivotal connection 26 of the first extension member 18 permits the angle $\alpha$ between the first extension member 18 and the first arm member 12 to be selectively increased and decreased, increasing and decreasing the range of motion. In a first position 28, the first extension member 18 is positioned at an angle $\alpha_1$, wherein the operative connection, at point "P," of the first and second extension members 18 and 20 is located in a plane "A" passing through the joint axis 16, wherein plane "A" is substantially orthogonal to a longitudinal axis of the first arm member 12. The first position 28 of point "P" provides a maximum angle of flexion of $\beta_1$. The second extension member stop 24 acts to limit the angle of maximum extension $\gamma_1$ between the second arm member 14 and the joint axis 16.

Figure 5:
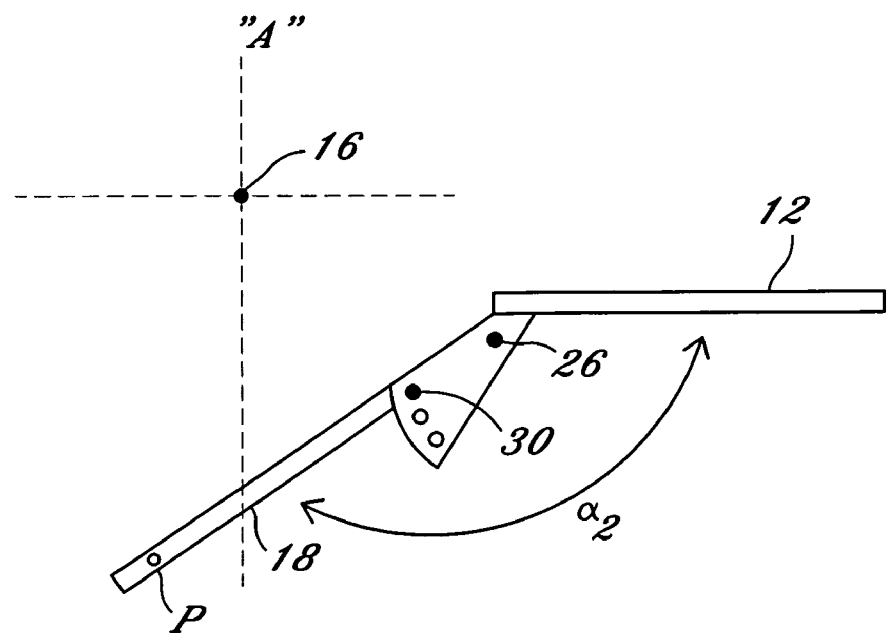
FIG. 5 shows the adjustable first extension member of FIG. 4 in a second position.

Referring to FIG. 5, in a second position 30 the angle $\alpha$ is increased to an angle $\alpha_2$, positioning the point "P" to a location "in front of" the plane "A." The second position 30 of point "P" provides a maximum angle of flexion of $\beta_2$, wherein $\beta_2$ is greater than $\beta_1$. The second extension member stop 24 acts to limit the angle of maximum extension $\gamma_2$ between the second arm member 14 and the joint axis, wherein $\gamma_2$ is less the $\gamma_1$.

The selective pivotal connection 26 of the first extension member 18 to the first arm member 12 can have a plurality of selectable positions. The angle $\alpha$ between the first arm member 12 and the first extension 18 can be selectively increased to move the point "P", on, "in front of" or "behind" the plane "A." It is also envisioned that a positioned can be selected to increase the angle $\alpha$ between the first arm member 12 and the first extension 18 sufficiently to move the point "P" "in front of" plane "A" and "above" the longitudinal axis of the first arm member 12, maximizing the maximum angle of flexion $\beta$.

The orthosis 10 of the present invention can be connected to the flexor side of the first and second body portions of the joint, which results in a decrease in angle as the joint is flexed (bent) and an increase in angle and the joint is extended (straightened). Alternatively, orthosis 10 of the present invention can be connected to the extensor side of the joint, which results in a decrease in angle as the joint is extended straightened and an increase in angle as the joint is flexed (bent).

Figure 6:
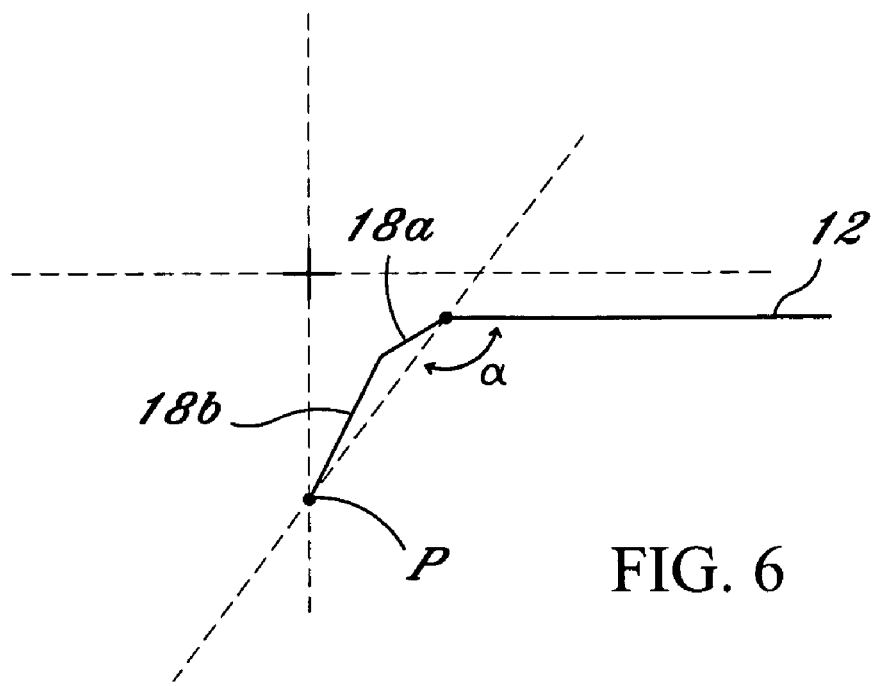
FIG. 6 shows a segmented first extension member of the present invention.
Figure 7:
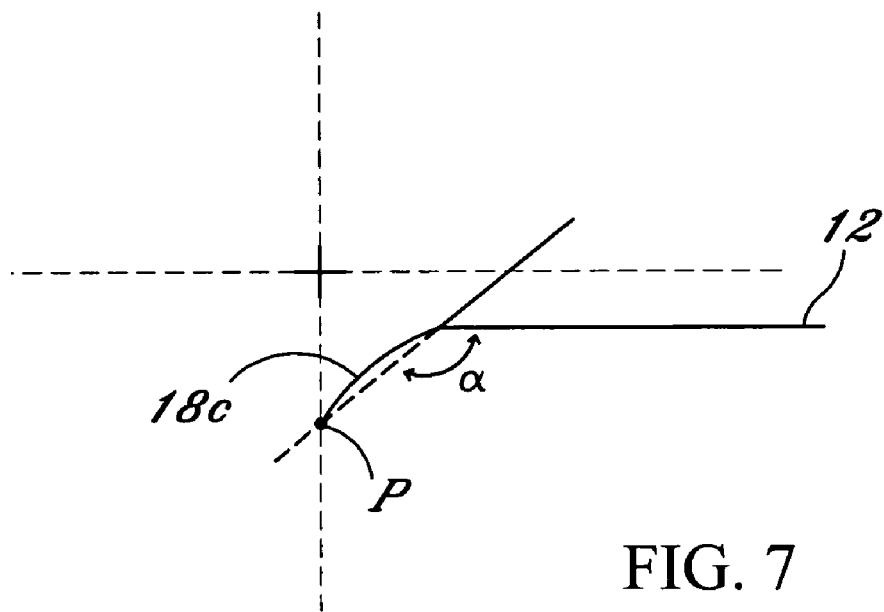
FIG. 7 shows an arcuate first extension member of the present invention.

The previous description of the first arm member 12 depicts a first extension 18 having a substantially linear shape, extending at an angle $\alpha$ from the first arm member 12. However, it is within the scope of the present invention that the first extension member 18 can be any shape extending from the first arm member 12 which positions the point "P" in the desired relationship to the plane "A." Referring to FIG. 6, a segmented fist extension member is shown, including a first extension member segment 18a and a second extension member segment 18b. The first and second extension member segments 18a and 18b extend from the first arm member 12, positioning the point "P" at an angle $\alpha$ from the first arm member 12. Referring to FIG. 7, an arcuate first extension member 18c is shown. The arcuate extension member 18c extends from the first arm member 12, positioning the point "P" at an angle $\alpha$ from the first arm member 12.

Figure 8:
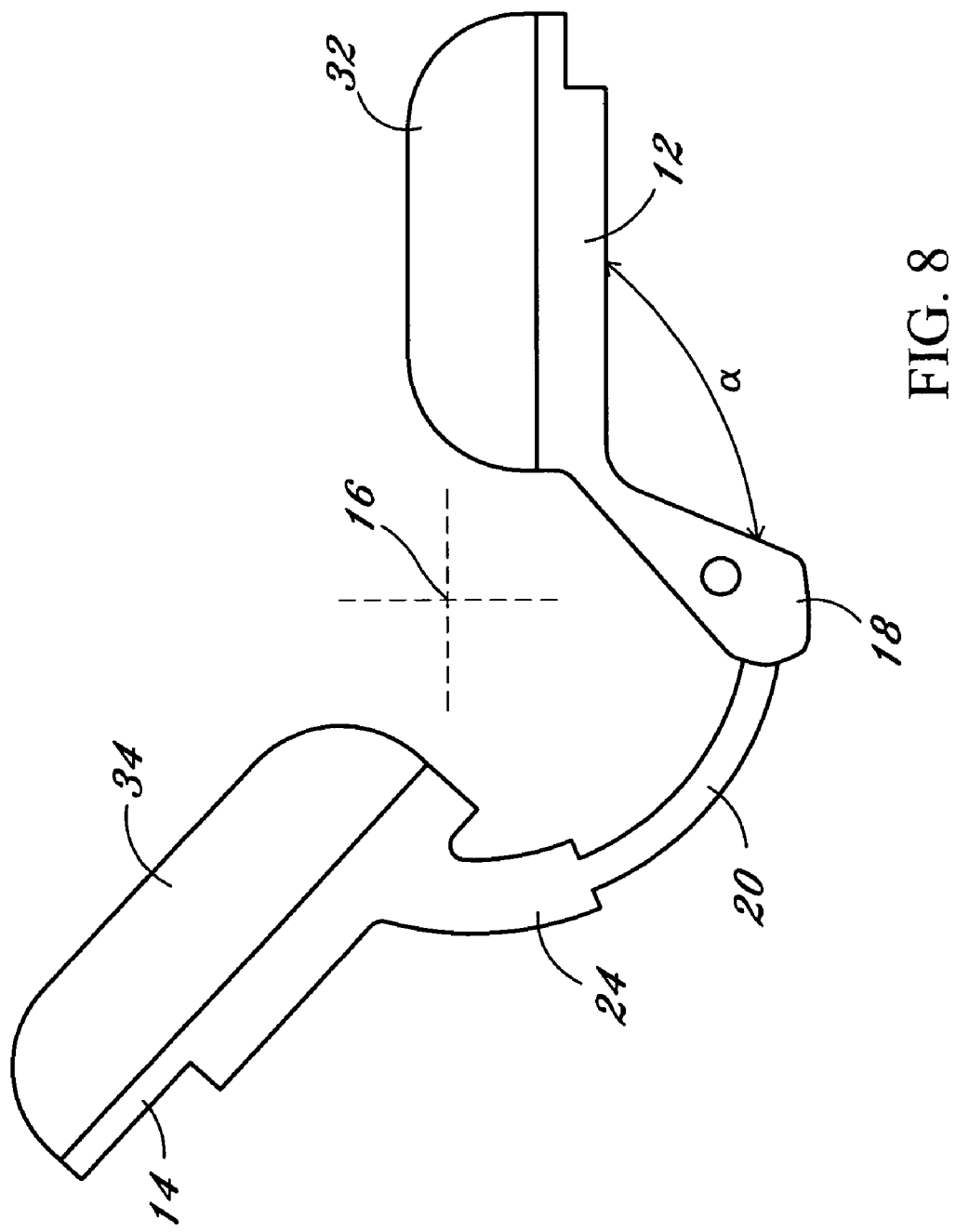
FIG. 8 shows an orthosis of the present invention.

Referring to FIG. 8, the orthosis 10 of the present invention includes a first arm member 12 attachable to the first body portion and a second arm member 14 attachable to the second body portion, wherein the joint axis 16 is interposed between and offset from the first and second arm members 12 and 14. The first and second arm members 12 and 14 are connected with each other offset from the joint axis 16.

The first arm member 12 of the orthosis 10 includes a first extension member 18, which extends at angle $\alpha$ from the first arm member 12. The second arm member 14 of the orthosis 10 includes a second extension member 20, having an arcuate shape. The first and second extension members 18 and 20 are operatively connected a point "P," such that in operation the second extension member 20 travels along an arcuate path about and substantially through point "P." The arcuate shape of the second extension member 20 results in the second body portion rotating about the joint axis 16, when the second arm member 14 is moved from a first position to a second position relative to the first arm member 12. The angle α between the first extension member 18 and the first arm member 12 and the radius of curvature of the second extension member 20 are a function of the joint to be treated and the degree of flexion or extension contractures.

A first cuff 32 is attached to the first arm member 12, wherein the first cuff 32 is positionable about the first body portion. The first cuff 32 is attached to the first body portion by cuff straps. The first cuff 32 secures the first body portion to the first arm member 12. A second cuff 34 is attached to the second arm member 14, wherein the second cuff 34 is positionable about the second body portion. The second cuff 34 is attached to the second body portion by cuff straps. The second cuff 34 secures the second body portion to the second arm member 14. (The term "cuff" as used herein means any suitable structure for transmitting the force of the orthosis 10 to the limb portion it engages.)

In an exemplary use, the orthosis 10 is operated to extend a joint in the following manner. The first cuff 32 is fastened about the first body portion tightly enough that the first arm member 12 may apply torque to the first body portion without having the first cuff 32 slide along the first body portion. Similarly, the second cuff 34 is fastened securely around the second body portion so that the second arm member 14 may apply torque to the second body portion without the second cuff 34 sliding along the second body portion. The orthosis 10 is attached to the first and second body portions in a first position. The second arm member 14 is rotated from the first position to a second position, relative to the first arm member 12, rotating the second body portion about the joint axis 16 stretching the joint. As the second arm member 14 is rotated to the second position, the second extension member 20 travels along an arcuate path about and substantially through point "P." The orthosis 10 is maintained in the second position for a predetermined treatment time providing a constant stretch to the joint. After the expiration of the treatment time, the second arm member 14 is moved back to the first position, relieving the joint. Optionally, the second arm member 14 can be rotated to a third position, increasing the stretch on the joint. The second arm member 14 can be rotated at discrete time intervals to incrementally increase the stretch of the joint through the treatment cycle. After completion of the treatment cycle, the second arm member is returned to the first position for removal of the orthosis 10.

The first and second arm members 12 and 14 are rigid members made of, for example, aluminum, stainless steel, polymeric, or composite materials. The arms are rigid so as to be able to transmit the necessary forces. It should be understood that any material of sufficient rigidity can be used.

In an embodiment, the components of the orthosis 10 of the present invention are made by injection molding. Generally for injection molding, tool and die metal molds of the orthosis 10 components are prepared. Hot, melted plastic material is injected into the molds. The plastic is allowed to cool, forming components. The components are removed from the molds and assembled. The cuff portions 32 or 34 can be individual molded and attached to the arm members 12 or 14. Alternatively, the cuff portions can be molded as an integrated part of the arm members 12 or 14.

In use, the orthosis 10 can be connected to the flexor side of the first and second body portions of the joint, which results in a decrease in angle as the joint is flexed (bent) and an increase in angle as the joint is extended (straightened). Alternatively, orthosis 10 of the present invention can be connected to the extensor side of the joint, which results in a decrease in angle as the joint is extended straightened and an increase in angle as the joint is flexed (bent).

In an embodiment, the orthosis 10 includes a first cuff 32 for attachment to a first body portion, and a second cuff 34 for attachment to a second body portion. The first body portion is joined to the second body portion at a joint, around which is located, as is well known, soft tissue. Each of the first and second cuffs 32 and 34 includes loop connectors for receiving straps extending around the body portions to clamp the cuffs 32 and 34 to the body portions.

The first cuff 32 is mounted for sliding movement on the first arm member 12 and is slidable along the first arm member 12 in a manner as described below. The second cuff 34 is mounted for sliding movement on a second arm member 14 and is slidable along the second arm member 12 in a manner as described below.

Bending a Joint in Extension:

In operation of the orthosis 10 to extend the joint, the orthosis 10 starts at a more flexed position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the joint.

As the orthosis 10 is rotated from the first position to the second position, extending the joint, the first and second cuffs 32 and 34 move along the first and second arm members 12 and 14. The first cuff 32 moves inwardly along the first arm member 12. Similarly, the second cuff 34 moves inwardly along the second arm member 14. Because the cuffs 32 and 34 are clamped onto the first and second body portions as described above, the outward pivoting movement of the first and second arm members 12 and 14 and the cuffs 32 and 34 causes the joint to be extended as desired. However, this extension of the joint can place strong distractive forces on the soft tissues around the joint. The sliding movement of the cuffs 32 and 34, inwardly along the first and second arm members 12 and 14, helps to limit these distractive forces by counteracting the outward movement of the first and second arm members 12 and 14. The cuffs 32 and 34 slide inwardly along the first and second arm members 12 and 14 a distance far enough so that the joint is only slightly distracted during extension. Thus, the detrimental effects of strong distractive forces normally generated in forced extension of a joint are avoided, being replaced with the beneficial effects of limited and controlled distraction.

Bending a Joint Flexion:

In operation of the orthosis 10 to flex the joint, the orthosis 10 starts at a more extended position. The first and second cuffs 32 and 34 are clamped onto the first and second body portions, respectively, by straps, tightly enough so that the cuffs 32 and 34 can apply torque to the body portions to extend the joint. The second arm member 14 is rotated from the first position to a second position, relative to the first arm member 12, rotating the second body portion about the joint axis 16 stretching the joint. As the second arm member 14 is rotated to the second position the second extension member 20 travels about and substantially though point "P," along an arcuate path. The orthosis 10 is maintained in the second position for a predetermined treatment time providing a constant stretch to the joint.

As the orthosis 10 is rotated from the first position to the second position, flexing the joint, the first and second cuffs 32 and 34 move along the first and second arm members 12 and 14. The first cuff 32 moves outwardly along the first arm member 12. Similarly, the second cuff 34 moves outwardly along the second arm member 14. Because the cuffs 32 and 34 are clamped onto the first and second body portions the inward pivoting movement of the first and second arm members 12 and 14 and the cuffs 32 and 34 causes the joint to be flexed as desired. However, this flexion of the joint can place strong compressive forces on the soft tissues around the joint. The sliding movement of the cuffs 32 and 34, outwardly along the first and second arm members 12 and 14, helps to limit these compressive forces by counteracting the inward movement of the first and second arm members 12 and 14. The cuffs 32 and 34 slide outwardly along the first and second arm members 12 and 14 a distance far enough so that the joint is only slightly compressed during flexion. Thus, the detrimental effects of strong compressive forces normally generated in forced flexion of a joint are avoided, being replaced with the beneficial effects of limited and controlled compression.

Figure 9:
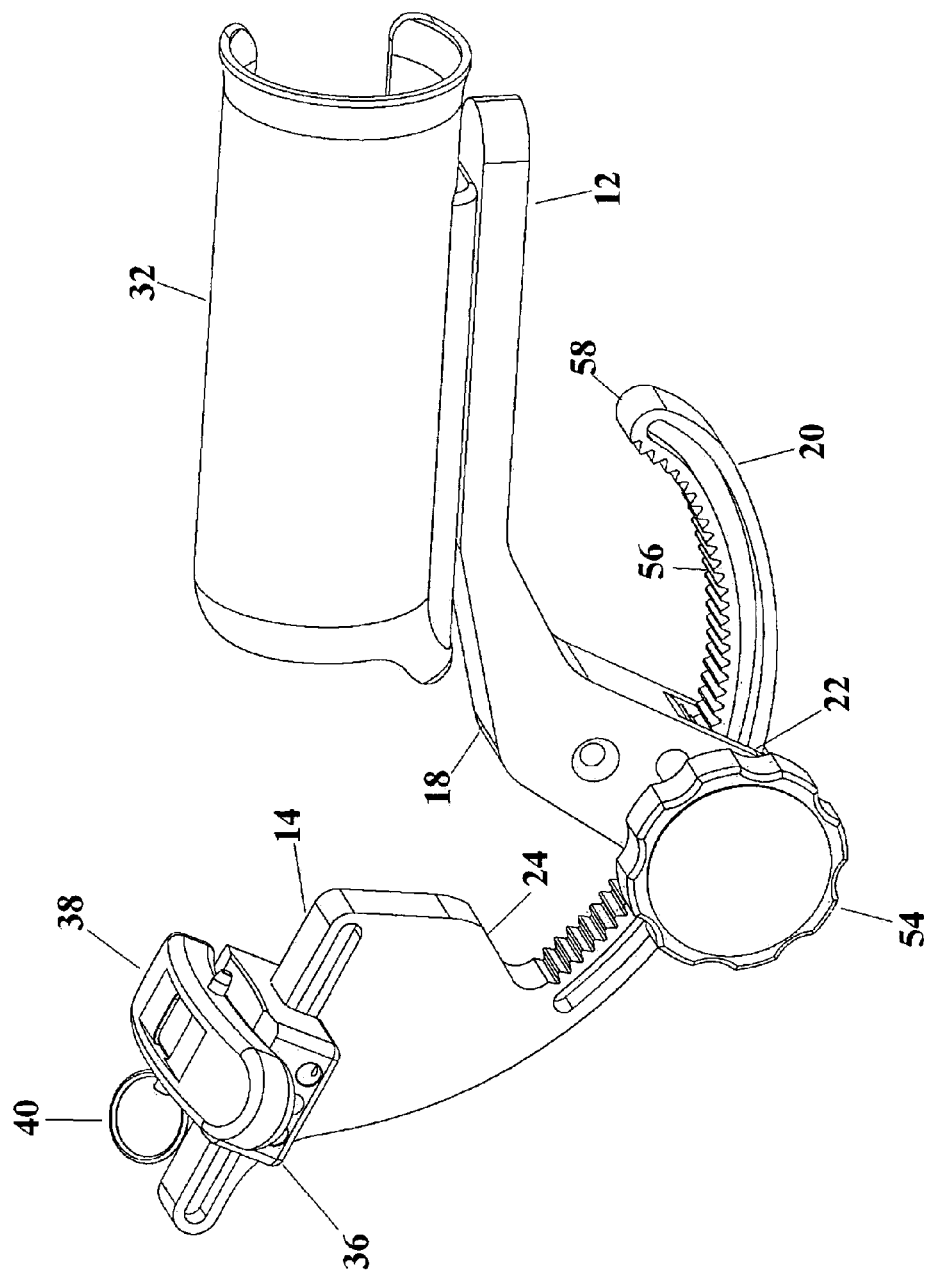
FIG. 9 shows an orthosis of the present invention for flexing and extending a wrist joint in a patient.

Referring now to FIG. 9, the orthosis 12 can be used to bend a wrist in flexion or extension. The orthosis 10 includes a first arm member 12 attachable to the forearm of a patient. The first cuff 32 is clamped onto the forearm by straps. A second arm member 14, operatively connected to the first arm member 12, is attachable to the hand of the patient, wherein the axis of the wrist joint is interposed between and offset from the first and second arm members 12 and 14. The second arm member 14 includes a base member 36 attach thereto. A hand pad 38 is attached to the base member 36. The hand pad 38 is clamped onto the hand by straps, tightly enough so that the second arm member 14 can apply torque to the joint. The hand pad 38 can be shaped to conform to the palm or the back surface of the hand.

Bending Wrist in Flexion:

When a wrist is to be bent in flexion, the first cuff 32 is connected with the forearm and the hand pad 38 is connected with the palm of the hand. The first cuff 32 and hand pad 38 are clamped onto the forearm and hand, respectively, by straps, tightly enough so that they can apply torque to flex the joint. The second arm member 14 is rotated from the first position to a second position, relative to the first arm member 12, rotating the hand about the wrist joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the wrist joint.

Bending Wrist in Extension:

When a wrist is to be bent in extension, the first cuff 32 is connected with the forearm and the hand pad 38 is connected with the back surface of the hand. The first cuff 32 and hand pad 38 are clamped onto the forearm and back surface of the hand, respectively, by straps, tightly enough so that they can apply torque to flex the joint. The second arm member 14 is rotated from the first position to a second position, relative to the first arm member 12, rotating the hand about the wrist joint axis 16 stretching the joint. As the second arm member 14 is rotated to the second position the second extension member 20 travels along an arcuate path about and substantially through point "P." The orthosis 10 is maintained in the second position for a predetermined treatment time providing a constant stretch to the wrist joint.

In an embodiment, the hand pad 38 is removable attached to the base member 36. The hand pad 38 includes a first surface, which has a substantially convex shape, to conform to the palm of the hand. A second surface, opposite the first surface, is also included, having a substantially concave shape, to conform to the back surface of the hand. The hand pad 38 can be removable attached to the base member 36 such that the first or second surfaces engages the hand of the patient.

For example, the hand pad 38 is removably secured to base member 36 by detent pin 40. The removable securing of the hand pad 38 allows the orthosis 10 to be used for both flexion and extension of the wrist. In flexion, the hand pad 38 is connected to the base member 36 with the first surface facing "up" to conform to the palm of the hand. In extension, the hand pad 38 is connected to the base member 36 with the second surface facing "up" to conform to the back surface of the hand.

The base member 38 can be mounted for sliding movement on the second arm member 14 and is slidable along the second arm member 14 in a manner as described below.

Bending Wrist in Extension:

In operation of the orthosis 10 to extend the wrist joint, the orthosis 10 starts at a more flexed position. The first cuff 32 is connected with the forearm and the hand pad 38 is connected with the palm of the hand. The first cuff 32 and hand pad 38 are clamped onto the forearm and palm of the hand so as to apply torque to extend the wrist joint. The second arm member 14 is rotated from the first position to a second position, relative to the first arm member 12, rotating the hand about the wrist joint axis 16 stretching the wrist joint. As the second arm member 14 is rotated to the second position the second extension member 20 travels along an arcuate path about and substantially through point "P." The orthosis 10 is maintained in the second position for a predetermined treatment time providing a constant stretch to the joint.

As the orthosis 10 is rotated from the first position to the second position, extending the joint, the base member 36 and hand pad 38 move along the second arm member 14. The base member 36 and hand pad 38 move inwardly along the second arm member 14. Because the cuff 32 and hand pad 38 are clamped onto the forearm and hand the outward pivoting movement of the first and second arm members 12 and 14 causes the joint to be extended as desired. However, this extension of the joint can place strong distractive forces on the soft tissues around the joint. The sliding movement of the base member 36 and hand pad 38, inwardly along the second arm member 14, helps to limit these distractive forces by counteracting the outward movement of the second arm members 12 and 14. The base member 36 and hand pad 38 slide inwardly along the second arm member 14 a distance far enough so that the joint is only slightly distracted during extension. Thus, the detrimental effects of strong distractive forces normally generated in forced extension of a joint are avoided, being replaced with the beneficial effects of limited and controlled distraction.

Bending Wrist in Flexion:

In operation of the orthosis 10 to flex the wrist joint, the orthosis 10 starts at a more extended position. The first cuff 32 is connected with the forearm and the hand pad 38 is connected with the back surface of the hand. The first cuff 32 and hand pad 38 are clamped onto the forearm and back surface of the hand so as to apply torque to flex the wrist joint. The second arm member 14 is rotated from the first position to a second position, relative to the first arm member 12, rotating the hand about the wrist joint axis 16 stretching the wrist joint. As the second arm member 14 is rotated to the second position the second extension member 20 travels along an arcuate path about and substantially through point "P." The orthosis 10 is maintained in the second position for a predefined treatment time providing a constant stretch to the joint.

As the orthosis 10 is rotated from the first position to the second position, flexing the joint, the base member 36 and hand pad 38 move along the second arm member 14. The base member 36 and hand pad 38 move outwardly along the second arm member 14. Because the cuff 32 and hand pad 38 are clamped onto the forearm and hand the inward pivoting movement of the first and second arm members 12 and 14 causes the joint to be flexed as desired. However, this flexing of the joint can place strong compressive forces on the soft tissues around the joint. The sliding movement of the base member 36 and hand pad 38, outwardly along the second arm member 14, helps to limit these compressive forces by counteracting the inward movement of the first and second arm members 12 and 14. The base member 36 and hand pad 38 slide outwardly along the second arm member 14 a distance far enough so that the joint is only slightly compressed during extension. Thus, the detrimental effects of strong compressive forces normally generated in forced flexion of a joint are avoided, being replaced with the beneficial effects of limited and controlled compression.

In the above description, the hand pad 38 is shown sliding inwardly and outwardly along the second arm member 14. However, it is contemplated that the hand pad 38 can slide in other directions. For example, the hand pad 38 can slide substantially orthogonal to the second arm member 14, wherein the substantially orthogonal directions can have an arcuate path. Similarly, as discussed in more detail below, it is contemplated within the scope of the present invention that hand pad 38 can be connected to the second arm member 14 such that hand pad 38 can exhibit both longitudinal and orthogonal motion (and combinations thereof) with respect to the second arm member 14.

In the above description, the second extension member 20 is shown and described as having a substantially circular arcuate shape, positioning the axis of rotation at the joint axis 16. However, it is contemplated that the second extension member 20 can have alternative shapes.

Figure 10:
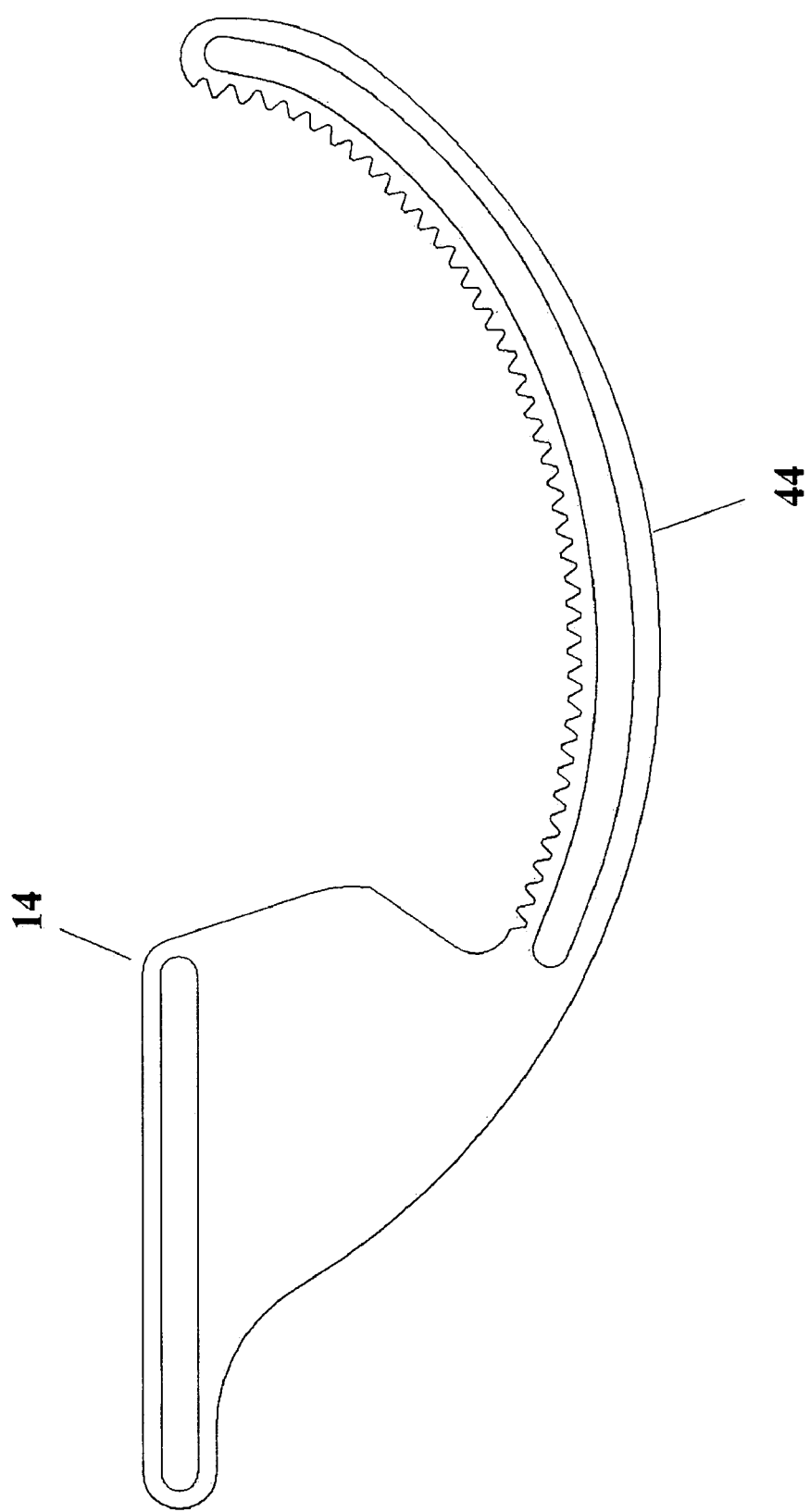
FIG. 10 shows a non-circular arcuate shaped second extension member of the present invention.

Referring to FIG. 10, the second arm member 14 is shown having a non-circular arcuate shaped second extension member 44. The non-circular arcuate shaped second extension member 44 provide an axis of rotation which changes as the second arm member 14 is moved from the first position to the second portion. As such, as the second arm member 14 is moved from the first position to the second portion the second body portion will exhibit both a rotational motion, about the joint axis 16, and a translational motion, distracting or compressing the joint.

Figure 11:
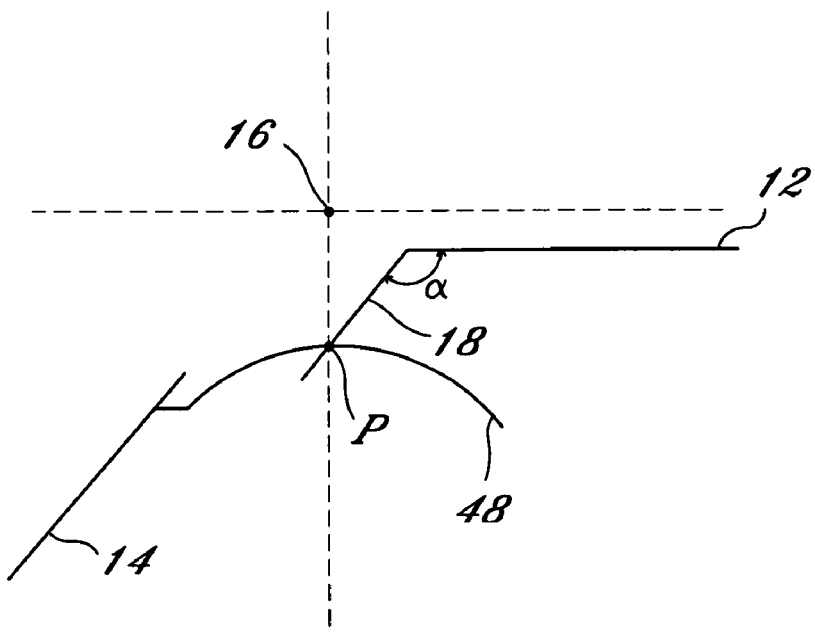
FIG. 11 shows an alternative arcuate shaped second extension member of the present invention.

In the previously described embodiments, the arcuate shape of the second extension member 20 or 44 as shown have concave radius of curvature relative to the joint 16. However, referring to FIG. 11, it is contemplated that the second extension member 18 or 44 can have a convex radius of curvature relative to the joint 16. Similar to the concave radius of curvature, the convex arcuate shape of the second extension member 18 or 44 results in the second body portion rotating about the joint axis 16, when the second arm member 14 is moved from a first position to a second position relative to the first arm member 12.

Figure 12:
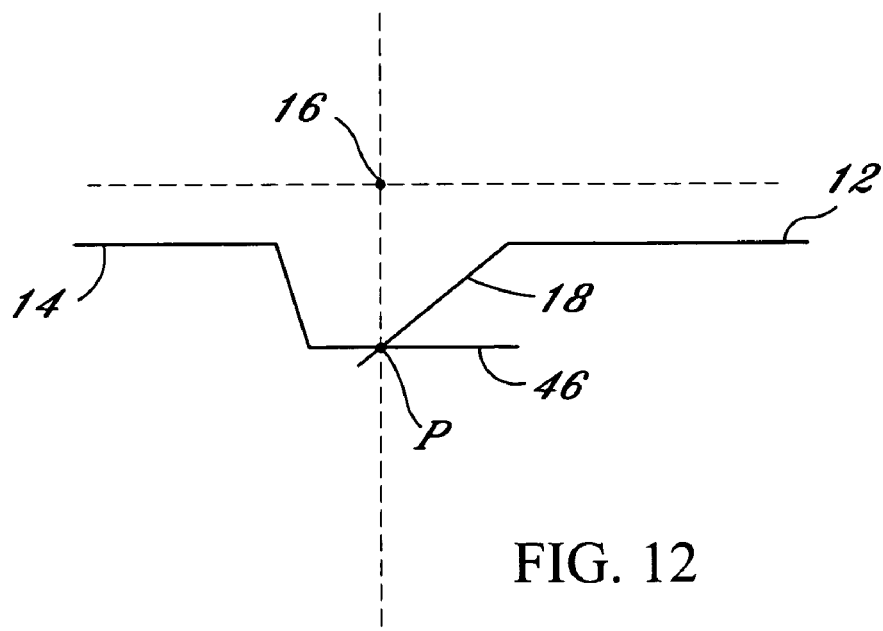
FIG. 12 shows a linear shaped second extension member of the present invention.

Referring to FIG. 12, the second arm member 14 of the orthosis 10 includes a second extension member 48 extending therefrom and having a linear shape. The first and second extension members 18 and 48 are operatively connected at point "P," such that in operation the second extension member 48 travels along a linear path through point "P." The linear shape of the second extension member 48 results in the second body portion being translated with respect to the first body portion. The translational movement of the second arm member 14 results is a distraction or compression of the joint when the second arm member 14 is moved from a first position to a second position relative to the first arm member 12.

As discussed further below, the hand pad can be mounted for translational and rotational movement on the base member.

Figure 13:
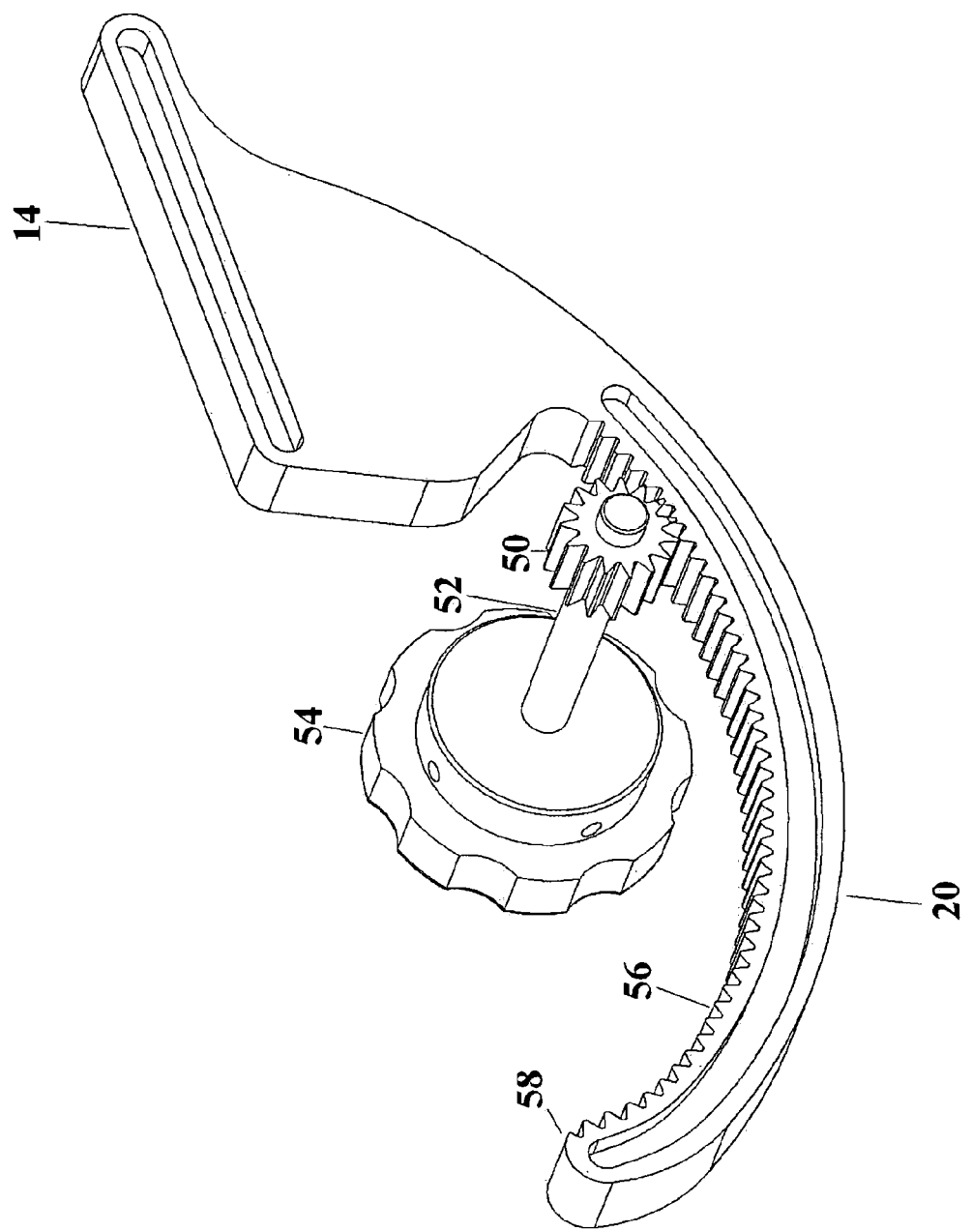
FIG. 13 shows an exemplary drive assembly of the present invention.

Drive Assembly:

Referring to FIGS. 9 and 13, the drive assembly 22 of the orthosis includes a gear system. As previously noted, the components of the orthosis, including the drive assembly 22, can be made by injection molding a polymer. The drive assembly 22 is supported in the first extension member 18, including a gear 50 rotatable about point "P." A shaft 52, attached to the gear 50, extends from first extension member 18. A knob 54 is connected to the shaft 52, opposite the gear 50, for manually rotating the gear 50. The second extension member 20 includes a series of teeth 56 along an inner surface 58. The second extension member 20 is threaded through the first extension member 18, such that the teeth 56 on the second extension member 20 engage the gear 55. The rotation of the knob 56 causes the gear 50 to rotate, pushing or pulling the second extension member 20 through the first extension member 18. The drive assembly 22 includes a locking or breaking mechanism which prevents the gear 50 from rotating absent am applied force rotation of the knob 46. Such a lock or breaking mechanism can include a compression washer or other known gear locking or breaking mechanisms.

The drive assembly 22 is described as utilizing a gear system. However, it is contemplated that other known drive systems can be used to move the second extension member 20 through the first extension member 18, for example a friction type drive system. Regardless of the drive system used, the joint orthosis of the present invention can act as a brace, restricting the relative movement of the first and second body portions to one degree of freedom (e.g. flexion and extension about the joint). Thus, drive assembly 22 can be configured to allow free motion in one degree of freedom. This can be achieved in a number of different ways. For example, gear 50 can be positioned such that it does not engage teeth 56.

In an alternative embodiment, the drive assembly 22 for an orthosis 10 in accordance with the present invention can be actuated by a motor instead of by a manually actuatable member, such as the knob 54.

In an embodiment, an electric motor is mounted to the shaft 52 for rotation of the gear 50. A battery provides electric power to the motor. Alternatively, the motor can be supplied with external power. A microprocessor controls the operation of the motor. The microprocessor and motor together can be used to cycle the first and second arm members 12 and 14 through extension and flexion; to move the first and second arm members 12 and 14 in one pivotal direction a certain amount, hold there while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. The programming and control of the microprocessor is within the skill of the art as it relates to driving the motor to control the first and second arm members 12 and 14 to move in known manners. This embodiment is ideally suited for continuous passive motion exercise, because the orthosis is portable and because the motor can be programmed with the desired sequence of movements.

It should be understood that the particular physical arrangement of the motor, the battery, and the microprocessor is not the only possible arrangement of those elements. The invention contemplates that other arrangements of these or similarly functional elements are quite suitable, and thus, the invention is intended to cover any such arrangement. Additionally, another type of power source, other than an electric motor, can also be used. For example, the use of a hydraulic or pneumatic motor as the drive mechanism is contemplated.

Figure 14:
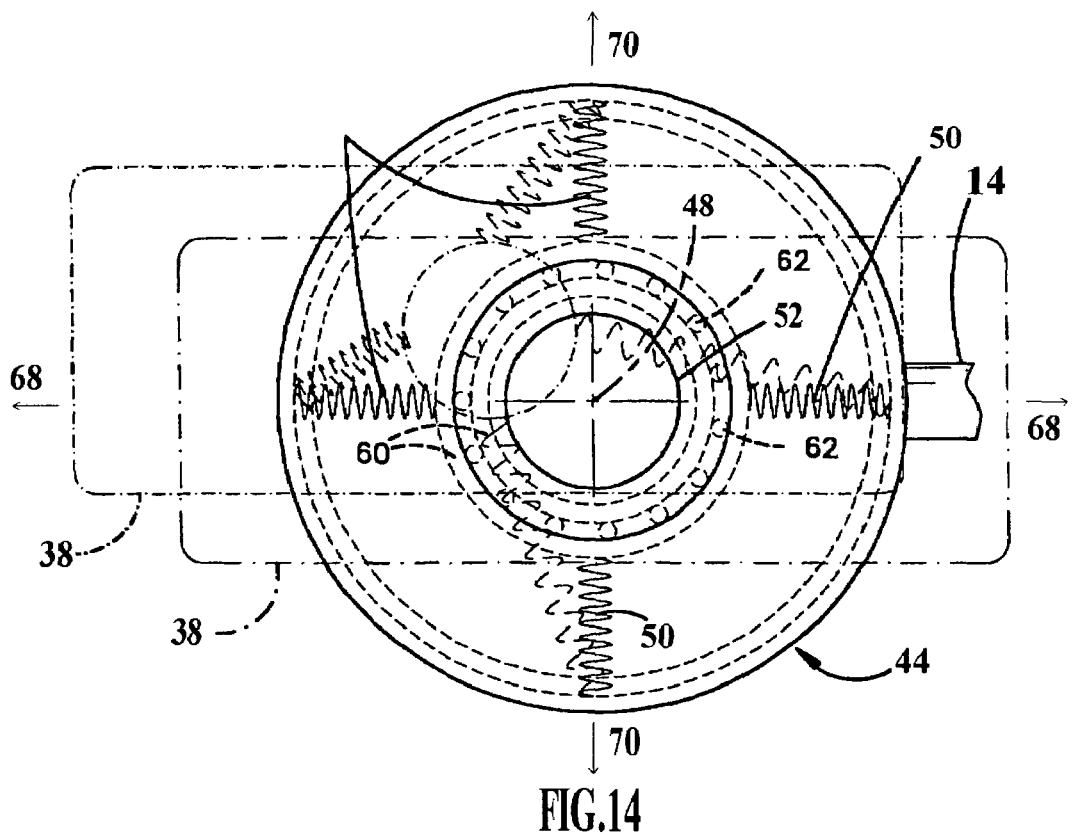
FIG. 14 is a top plan view of portions of an articulating hand pad support of the present invention.
Figure 15:
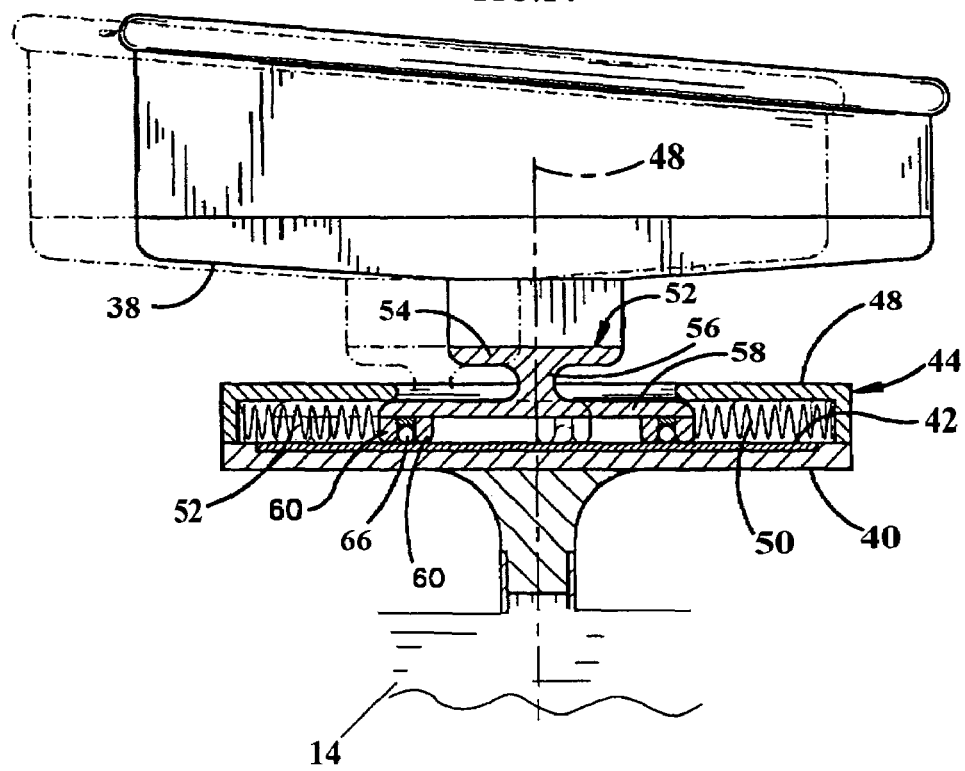
FIG. 15 is a schematic sectional view of the articulating hand pad support of FIG. 14.

Referring to FIGS. 14 and 15, another embodiment in which the hand pad 38 articulates with respect to the second arm member 14 is shown. The second arm member 14 has a circular base member 40 attached thereto. The circular base member 40 supports a circular base plate 42. A circular cover 44 extends upwardly from the circular base member 40 and has a portion 46 extending radially inwardly toward a vertical axis 48 to define a slide chamber 50.

A hand pad support slider 52 is received in the slide chamber 50. The support slider 52 has an upper portion 54 to which the hand pad 38 is attached. The upper portion 54 is connected by a neck 56 to a circular planar portion 58. Two annular bearing races 60 extend downwardly from the planar portion 58 and secure between them a plurality of ball bearings 62. A washer 64 is disposed above the bearings 62. The ball bearings 62 support the slider 52 and thus the hand pad 38 for sliding movement in any direction within the slide chamber 50. The hand pad 38 can be made self-centering by springs 66.

Thus, the hand pad 38 is slidable relative to the circular base member 40 in any direction for a limited extent. As indicated by the arrow 68, the hand pad 38 is slidable fore and aft within the extent of travel allowed by the support slider 52 within the slide chamber 50. As indicated by the arrow 70, the hand pad 38 is slidable laterally within the extent of travel allowed by the support slider 52 within the slide chamber 50. With these two combined, it can be seen that the roller bearing assembly provides a compound of movement of the hand pad 38.

It will be appreciated by persons skilled in the art that the present invention is not limited to what has been particularly shown and described herein above. For example, although the examples presented identify the wrist joint, the present invention can be used for any joint. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An orthosis for stretching tissue around a joint of a patient between first and second relatively pivotable body portions, comprising:
   a first arm member affixable to the first body portion and including a first extension member extending therefrom;
   a second arm member affixable to the second body portion and including a second extension member having an arcuate shape extending therefrom, the second extension member is operatively connected to the first extension member and travels along an arcuate path through the first extension member when the second arm member is moved from a first position to a second position relative to the first arm member, wherein the arcuate path and the joint lie in a plane substantially orthogonal to an axis of rotation of the joint.

2. The orthosis of claim 1, further comprising a first cuff attached to the first arm member.

3. The orthosis of claim 2, wherein the first cuff is fastenable about the first body portion tightly enough that the first arm member may apply a force to the first body portion without having the first cuff slide along the first body portion.

4. The orthosis of claim 2, wherein the first cuff is slidably mounted to the first arm member.

5. The orthosis of claim 1, further comprising a second cuff attached to the second arm member.

6. The orthosis of claim 5, wherein the second cuff is fastenable about the second body portion tightly enough that the second arm member may apply a force to the second body portion without having the second cuff slide along the second body portion.

7. The orthosis of claim 5, wherein the second cuff is slidably mounted to the second arm member.

8. The orthosis of claim 1, further comprising a hand pad attached to the second arm member.

9. The orthosis of claim 8, wherein the second body portion is a hand of the patient and the hand pad is fastenable about the hand of the patient tightly enough that the second arm member may apply a force to the hand of the patient without having the hand pad slide along the hand of the patient.

10. The orthosis of claim 8, wherein the hand pad includes a convex surface for engaging a palm portion of the hand of the patient.

11. The orthosis of claim 8, wherein the hand pad includes a concave surface for engaging a back surface of the hand of the patient.

12. The orthosis of claim 8, wherein the hand pad is articulatingly mounted to the second arm member.

13. The orthosis of claim 8, wherein the hand pad is selectively, removably attached to the second arm member.

14. The orthosis of claim 13, wherein the hand pad includes a convex surface for engaging a palm portion of the hand of the patient.

15. The orthosis of claim 13, wherein the hand pad includes a concave surface for engaging a back surface of the hand of the patient.

16. The orthosis of claim 1, further comprising a drive assembly on the first extension member, the drive assembly engaging the second extension member for selectively roving the second arm member with respect to the first arm member.

17. The orthosis of claim 16, wherein the drive assembly includes a gear rotatably mounted in the first extension member.

18. The orthosis of claim 17, further comprising a motor operatively connected to the gear for selectively moving the second arm member with respect to the first arm member.

19. The orthosis of claim 17, wherein the second extension member includes a plurality of teeth for engaging the gear.

20. The orthosis of claim 19, wherein the gear is manually rotatable for selectively moving the second arm member with respect to the first arm member.

21. The orthosis of claim 1, wherein the joint defines a first plane substantially orthogonal to a longitudinal axis of the first arm member and a second plane substantially parallel to the longitudinal axis of the first arm member.

22. The orthosis of claim 21, wherein the first extension member extends from the first arm member, such that the operative connection of the first and second extension members lies in the first plane.

23. The orthosis of claim 21, wherein the first extension member extends from the first arm member, such that the operative connection of the first and second extension members is in front of the first plane.

24. The orthosis of claim 21, wherein the first extension member extends from the first arm member, such that the operative connection of the first and second extension members is behind the first plane.

25. The orthosis of claim 1, wherein the first extension member is selectively, pivotably connected to the first arm member.

26. An orthosis for stretching tissue around a joint of a patient between first and second relatively pivotable body portions, comprising:
a first arm member affixable to the first body portion and including a first extension member extending therefrom;
a second arm member affixable to the second body portion and including a second extension member having an arcuate shape extending therefrom, the second extension member is operatively connected to the first extension member and travels along an arcuate path through the first extension member when the second arm member is moved from a first position to a second position relative to the first arm member; and
a hand pad attached to the second arm member, wherein the hand pad is slidably mounted to the second arm member.

27. An orthosis for stretching tissue around a joint of a patient between first and second relatively pivotable body portions, comprising:
a first arm member affixable to the first body portion and including a first extension member extending therefrom; and
a second arm member affixable to the second body portion and including a second extension member having an arcuate shape extending therefrom, the second extension member is operatively connected to the first extension member and travels along an arcuate path through the first extension member when the second arm member is moved from a first position to a second position relative to the first arm member, wherein the joint and the first and second body portions defining on one side of the joint an inner sector which decreases in angle as the joint is flexed and defining on the opposite side of the joint an outer sector which decreases in angle as the joint is extended, such that the operative connection of the first and second extension members is located in the outer sector.

28. An orthosis for stretching tissue around a joint of a patient between first and second relatively pivotable body portions, the joint and the first and second body portions defining on one side of the joint an inner sector which decreases in angle as the joint is flexed and defining on the opposite side of the joint an outer sector which decreases in angle as the joint is extended, comprising:
a first arm member affixable to the first body portion and including a first extension member extending at an angle α therefrom;
a second arm member affixable to the second body portion and including a second extension member having an arcuate shape extending therefrom, the second extension member operatively connected to the first extension member and traveling through the first extension member along an arcuate path when the second arm member is moved from a first position to a second position relative to the first arm member, wherein the operative connection of the first and second extension members is located in the outer sector; and
a drive assembly on the first extension member, the drive assembly engaging the second extension member for selectively moving the second arm member with respect to the first arm member.

* * * * *